United States Patent [19]

Kume et al.

[11] Patent Number: 4,845,230

[45] Date of Patent: Jul. 4, 1989

[54] 2,5-DIHYDROPYRROLES

[75] Inventors: Toyohiko Kume, Hino; Toshio Goto, Machida; Atsumi Kamochi, Hino; Akihiko Yanagi, Oume; Shigeki Yagi, Tokyo; Hiroshi Miyauchi, Hachioji, all of Japan

[73] Assignee: Nihon Tokushu Noyaku Seizo K.K., Tokyo, Japan

[21] Appl. No.: 275,152

[22] Filed: Nov. 22, 1988

Related U.S. Application Data

[62] Division of Ser. No. 166,340, Mar. 9, 1988.

[30] Foreign Application Priority Data

Mar. 13, 1987 [JP] Japan ................................ 62-56926

[51] Int. Cl.$^4$ ............................................ C07D 417/04

[52] U.S. Cl. ................................................... 548/139

[58] Field of Search ........................................ 548/134

[56] References Cited

U.S. PATENT DOCUMENTS 3,981,714 9/1976 Metzger ............................. 548/139

4,138,243 2/1979 Bohner ................................... 71/94

FOREIGN PATENT DOCUMENTS 2263247 10/1975 France ............................... 548/139

2278696 2/1976 France ............................... 548/139

2347264 11/1977 France ............................... 548/139

2400013 3/1979 France ............................... 548/139

*Primary Examiner*—Robert Gerstl

*Attorney, Agent, or Firm*—Sprung, Horn, Kramer & Woods

[57] ABSTRACT

Herbicidally active novel 2,5-dihydropyrroles of the formula

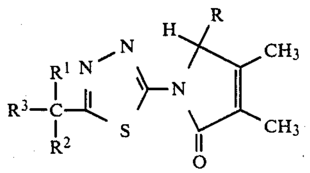

wherein $R^1$ represents a hydrogen atom or an alkyl group having 1 to 4 carbon atoms, $R^2$ and $R^3$ each represent an alkyl group having 1 to 4 carbon atoms or a haloalkyl group having 1 to 4 carbon atoms or together may form a $C_2$–$C_6$ alkylene group which may be substituted by halogen, and R represents a hydroxy group, a mercapto group, a halogen atom, an amino group or a group of the formula —O—W in which W represents an alkylcarbonyl, a halogenoalkylcarbonyl, an alkoxycarbonyl or a halogenoalkoxycarbonyl group each having 1 to 4 carbon atoms in the alkyl group, an alkylsulfonyl or a halogenoalkylsulfonyl group each having 1 to 4 carbon atoms in the alkyl group or a di-$C_1$–$C_4$-alkylamino sulfonyl group.

1 Claim, No Drawings

2,5-DIHYDROPYRROLES

This is a division of application Ser. No. 166,340, filed Mar. 9, 1988.

The present invention relates to novel 2,5-dihydropyrroles, to several processes for their preparation, and to their use as selective herbicide.

It has already been disclosed that certain 2,5-dihydropyrroles are useful as a pest controlling agent (see Japanese Laid-Open Patent Publication No. 23965/1978, corresponding to DE-OS 27 35 841 or U.S. Pat. No. 4,138,243).

There have now been found novel 2,5-dihydropyrroles of the formula (I)

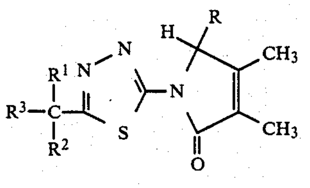
(I)

wherein $R^1$ represents a hydrogen atom or an alkyl group having 1 to 4 carbon atoms, $R^2$ and $R^3$ each represent an alkyl group having 1 to 4 carbon atoms or a haloalkyl group having 1 to 4 carbon atoms or together may form a $C_2$-$C_6$ alkylene group which may be substituted by halogen, and R represents a hydroxy group, a mercapto group, a halogen atom, an amino group or a group of the formula —O—W in which W represents an alkylcarbonyl, a halogenoalkylcarbonyl, an alkoxycarbonyl or a halogenoalkoxycarbonyl group each having 1 to 4 carbon atoms in the alkyl group, an alkylsulfonyl or a halogenoalkylsulfonyl group each having 1 to 4 carbon atoms in the alkyl group or a di-$C_1$-$C_4$-alkylamino sulfonyl group.

2,5-Dihydropyrroles of the formula (I) are obtained when (a) in the case where R in the formula (I) is hydroxy: compounds of the formula (II)

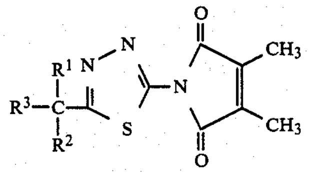
(II)

wherein $R^1$, $R^2$ and $R^3$ have the abovementioned meaning, are reacted with a reducing agent in the presence of inert solvents, or (b) in the case where R in the formula (I) is a halogen atom: 2,5-dihydropyrroles of the formula (Ia)

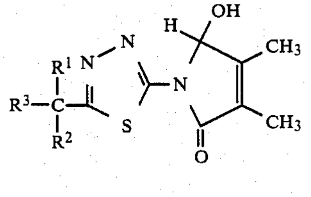
(Ia)

wherein $R^1$, $R^2$ and $R^3$ have the abovementioned meaning, are reacted with a halogenation agent in the presence of inert solvents, or (c) in the case where R in the formula (I) is the group —O—W: 2,5-dihydropyrroles of the aforementioned formula (Ia) are reacted with compounds of the formula (III)

W—Hal (III)

wherein

W has the abovementioned meaning, and

Hal represents halogen, or with compounds of the formula (IV)

W—O—W (IV)

wherein W has the abovementioned meaning, in the presence of inert solvents, if appropriate in the presence of acid binders, or (d) in the case where R in the formula (I) is a mercapto group: 2,5-dihydropyrroles of the formula (Ib)

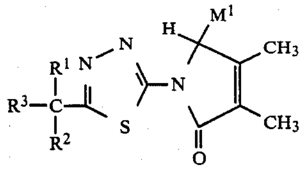
(Ib)

wherein $R^1$, $R^2$ and $R^3$ have the abovementioned meaning, and $M^1$ represents halogen, are reacted with potassium hydrogen sulfide, thiourea or N,N-dimethylthioformamide in the presence of inert solvents.

The novel 2,5-dihydropyrroles exhibit powerful and selective herbicidal properties.

Surprisingly, the 2,5-dihydropyrroles according to the invention exhibit a substantially greater selective herbicidal action than those known from the prior art, for instance, aforementioned Japanese Laid-Open Patent Publication No. 23965/1978, and at the same time have good compatibility to crops.

Among the 2,5-dihydropyrroles according to the invention, of the formula (I), preferred compounds are those in which $R^1$ represents methyl or ethyl, each $R^2$ and $R^3$ represent methyl, ethyl or a chloro- or fluoro-substituted $C_1$-$C_2$-alkyl group, and R represents hydroxy, mercapto, chloro, acetyloxy, methanesulfonyloxy or trifluoroacetyloxy.

Specifically, the following compound may be mentioned: N-(5-tert-butyl-1,3,4-thiadiazol-2-yl)-3,4-dimethyl-2-hydroxy-5-oxo-2,5-dihydropyrrole.

When in the process (a), if, for example, N-(5-tert-butyl-1,3,4-thiadiazol-2-yl)-2,3-dimethylmaleinimide and sodium borohydride are used as starting materials, the course of the reaction can be represented by the following equation:

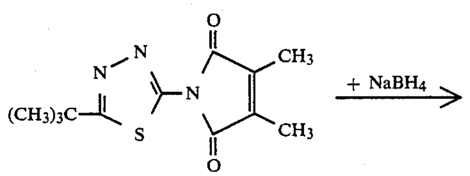

-continued

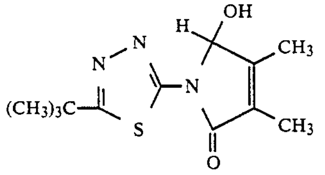

When in the process (b), if, for example, N-(5-tert-butyl-1,3,4-thiadiazol-2-yl)-3,4-dimethyl-2-hydroxy-5-oxo-2,5-dihydropyrrole and thionyl chloride are used as starting materials, the course of the reaction can be represented by the following equation:

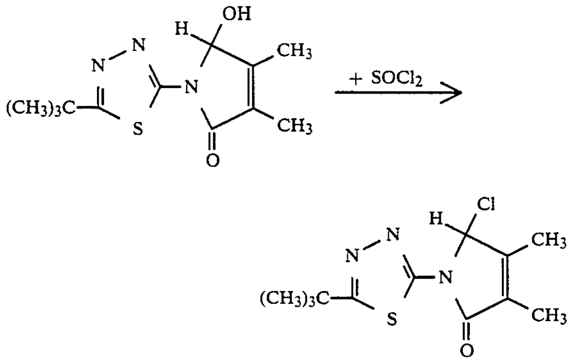

When in the process (c), if, for example, N-(5-tert-butyl-1,3,4-thiadiazol-2-yl)-3,4-dimethyl-2-hydroxy-5-oxo-2,5-dihydropyrrole and acetyl chloride are used as starting materials, the course of the reaction can be represented by the following equation:

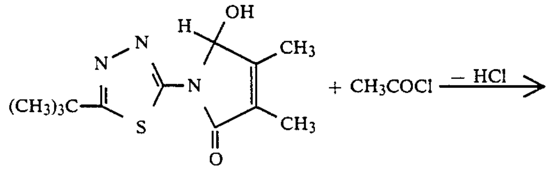

-continued

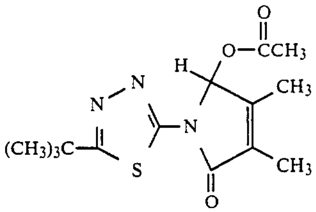

When in the process (d), if, for example, N-(5-tert-butyl-1,3,4-thiadiazol-2-yl)-3,4-dimethyl-2-chloro-5-oxo-2,5-dihydropyrrole and N,N-dimethylthioformamide are used as starting materials, the course of the reaction can be represented by the following equation:

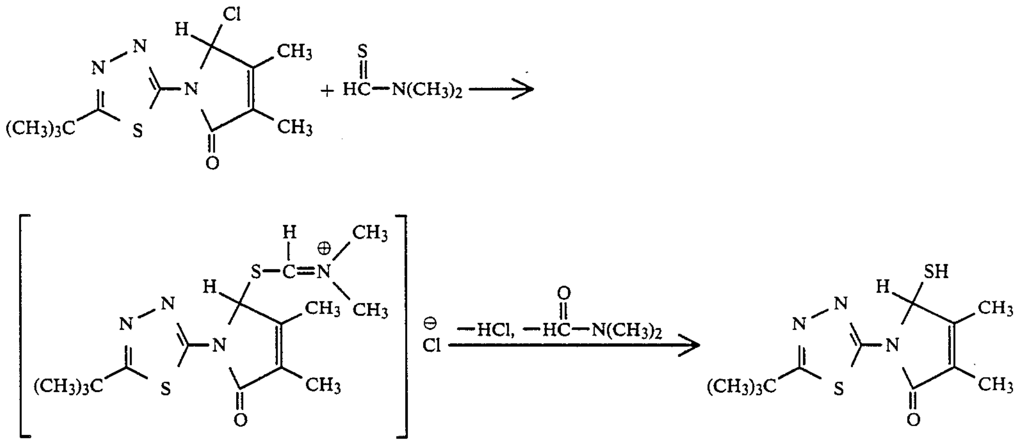

In the process (a), the starting compound of the formula (II) means compounds based on the above definitions of $R^1$, $R^2$ and $R^3$, preferably compounds based on the above preferred definitions.

The compounds of the formula (II) are novel compounds, and can be obtained, when compounds of the formula (V)

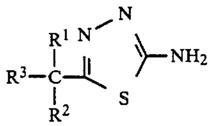

(V)

wherein $R^1$, $R^2$ and $R^3$ have the abovementioned meaning, are reacted with compounds of the formula (VI)

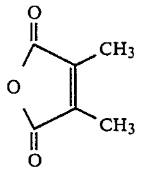

(VI)

or with 2 moles, per mole of the compound of formula (V), of maleic anhydride.

The compounds of the formula (V) are known. One specific example is 2-amino-5-tert-butyl-1,3,4-thiadiazol described in Can. J. Chem., vol. 37, pages 1121–1123, 1959.

2,3-Dimethylmaleic anhydride of the formula (VI) is described, for example, in Japanese Laid-Open Patent Publication No. 23965/1978. A specific example of the compound of the formula (II) is N-(5-tert-butyl-1,3,4-thiadiazol-2-yl)-dimethylmaleinimide.

Metal hydrides such as sodium borohydride and lithium aluminum hydride can be cited as examples of the reducing agent in the process (a).

The starting compounds of the formula (Ia) used in the process (b) are included within the compounds of the formula (I) that can be produced by the process (a).

Thionyl chloride can be cited as an example of the halogenating agent used in the process (b).

In process (c), the starting compounds of the formula (III) or (IV) mean compounds based on the definitions of W and Hal, and preferably, W represents an acetyl group and Hal represents a chlorine atom.

Acetyl chloride can be cited as a specific example of the compounds of the formula (III) which are well known.

The compounds of the formula (IV) are also well known, and acetic anhydride can be cited as one specific example.

All inert solvents are suitable diluents which are used in the practice of the process (a).

Examples of such diluents include, water, ethers (e.g., dioxane and tetrahydrofuran), alcohols (e.g., methanol, ethanol, isopropanol, butanol and ethylene glycol), and acid amides (e.g., dimethylformamide).

The process (a) can be practiced at temperatures within a substantially broad range, for example, at about −20° C. to about 80° C., preferably about 0° C. to about 30° C.

The reaction is desirably carried out under atmospheric pressure, but can also be carried out under elevated or reduced pressure.

In performing the process (a), the desired compounds of the formula (I) can be easily obtained by reducing the compounds of the formula (II) with the above-exemplified reducing agent, as shown in a working example given hereinafter.

In the practice of the process (b), hydrocarbons (e.g., benzene, toluene and xylene), and halogen-containing hydrocarbons (e.g., methylene chloride, chloroform, carbon tetrachloride, 1,2-dichloroethane and chlorobenzene) may be cited as suitable diluents.

The process (b) can be carried out at temperatures within a substantially broad range, for example, about −20° C. to about 150° C., preferably about 0° C. to about 80° C.

The reaction is carried out desirably under atmospheric pressure, but it is also possible to operate under elevated or reduced pressure.

In the practice of the process (b), the desired compounds of the formula (I) can be easily obtained by, for example, chlorinating the compounds of the formula (Ia) with thionyl chloride.

In the practice of the process (c), ethers (e.g., dioxane and tetrahydrofuran), acid amides (such as dimethylformamide, dimethylacetamide and hexamethylphosphoric triamide), and sulfoxides (such as dimethyl sulfoxide) may be cited as suitable diluents.

The process (c) can be carried out in the presence of an acid binder. Examples of such an acid binder include hydrides, hydroxides, carbonates, bicarbonates and alcoholates of alkali metals, and tertiary amines such as triethylamine, diethylaniline, pyridine, 4-dimethylaminopyridine, 1,8-diazabicyclo[5,4,0]-undecene (DBU) and 1,4-diazabicyclo-[2.2.2.]-octane (DABCO).

The process (c) can be carried out at temperatures over a substantially broad range, for example about 50° C. to about 200° C., preferably about 80° C. to about 160° C.

The reaction is desirably carried out under atmospheric pressure, but it is also possible to operate under elevated or reduced pressure.

In performing the process (c), the desired compounds of the formula (I) can be obtained, for example, by reacting 1 mole of the compounds of the formula (Ia) with 1 to about 1.5 moles of the compounds of the formula (III) or (IV) in an inert solvent in the optional presence of the acid binder.

In the practice of the process (d), alcohols (e.g. methanol, ethanol, isopropanol), aromatic hydrocarbons (e.g. benzene, toluene, xylene), amides (e.g. N,N-dimethylformamide, N,N-dimethylacetamide, 1-methyl-2-pyrrolidinone) and sulfoxides (e.g. dimethylsulfoxide, sulfolane) may be cited as suitable diluents.

The process (d) can be carried out at temperatures within a substantially broad range, for example, about 50° C. to about 160° C., preferably about 60° C. to about 130° C.

The reaction is desirably carried out under atmospheric pressure, but it is also possible to operate under elevated or reduced pressure.

In performing the process (d), the desired compounds of the formula (I) can be obtained, for example, by reacting 1 mole of the compounds of the formula (Ib) with 1 to about 1.2 moles of N,N-dimethylthioformamide in the presence of inert solvents, mentioned above.

The active compounds according to the invention can be used as defoliants, desiccants, agent for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossipium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloao, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use of seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl naphthalene, chlorinated aromatic or chlorinated aliphatic hydrocarbons, such as chlorobenzenes, chloroethylenes, or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl-formamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese boron, copper, cobalt, molybdenum and zinc.

The formulations in general from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known compounds, such as herbicides, fungicides, insecticides, acaricides, nematicides, bird repellents, plant nutrients and agents which improve soil structure, are also possible.

The active compounds can be used as such, in the form of their formulations or in the use form prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.001 and 4 kg of active compound per hectare of soil surface, preferably between 0.05 and 2 kg per ha.

The preparation and use of the active compounds according to the invention can be seen from the following examples.

PRODUCTION EXAMPLES

Example 1

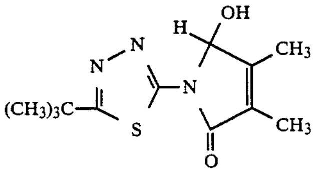

(compound No. 1)

Sodium borohydride (0.07 g) was added at room temperature to a methanol solution (100 ml) of N-(5-tert-butyl-1,3,4-thiadiazol-2-yl)-2,3-dimethylmaleinimide (0.95 g), and the mixture was stirred for 3 hours. After the reaction, glacial acetic acid (0.5 ml) was added and the solvent was evaporated under reduced pressure. Water (30 ml) was added to the residue, and potassium carbonate was added to make the mixture alkaline. It was extracted with dichloromethane (50 ml×2). The extractants were dried over anhydrous magnesium sulfate, and the solvent was evaporated under reduced pressure. The resulting crude crystals were washed with a small amount of diethyl ether to give the desired N-(5-tert-butyl-1,3,4-thiadiazol-2-yl)-3,4-dimethyl-2- hydroxy-5-oxo-2,5-dihydropyrrole (0.74 g), mp. 179°-182° C.

Table 1 below shows compounds of the invention which may be obtained by the same method as above.

TABLE 1

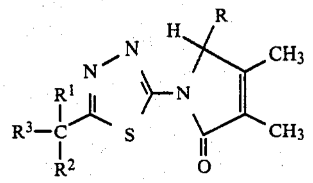

| Compound No. | $R^1$<br>$R^3$—C—<br>$R^2$ | R | physical properties |
|---|---|---|---|
| 2 | $-C(CH_3)_3$ | $-OCOCH_3$ | $n_D^{20}$ 1.5290 |
| 3 | $-C(CH_3)_3$ | —Cl | mp. 78-80° C. |
| 4 | $C_2H_5$<br>$-C(CH_3)_2$ | —OH | mp. 128-131° C. |
| 5 | $CH_3$<br>$-C(C_2H_5)_2$ | —OH | mp. 128-130° C. |
| 6 | $CH_2Cl$<br>$-C(CH_3)_2$ | —OH | mp. 155-156° C. |
| 7 | $CH_2F$<br>$-C(CH_3)_2$ | —OH | mp. 180-181° C. |
| 8 | $CH_3$<br>$-C(CH_2Cl)_2$ | —OH | |
| 9 | $CH_3$<br>$-C(CH_2F)_2$ | —OH | |
| 10 | $CHCl_2$<br>$-C(CH_3)_2$ | —OH | |
| 11 | $CHF_2$<br>$-C(CH_3)_2$ | —OH | |
| 12 | $C(CH_3)_3$<br>$-C(CH_3)_2$ | —OH | |
| 13 | 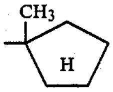 | —OH | |
| 14 | 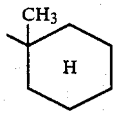 | —OH | |
| 15 | 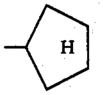 | —OH | mp. 197-198° C. |
| 16 | $-C(CH_3)_3$ | —SH | |
| 17 | $C_2H_5$<br>$-C(CH_3)_2$ | —Cl | |

TABLE 1-continued

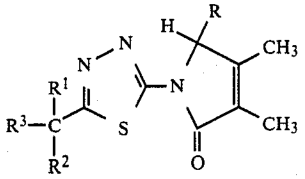

| Compound No. | $R^1$<br>$R^3$—C—<br>$R^2$ | R | physical properties |
|---|---|---|---|
| 18 | 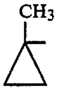 | OH | |
| 19 | 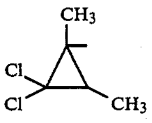 | OH | |
| 20 | $(CH_3)_3C-$ | $OCOCH_2Cl$ | m.p. 116-118° C. |
| 21 | $(CH_3)_3C-$ | $OCOCF_3$ | viscous oil |
| 22 | $(CH_3)_3C-$ | $OSO_2CH_3$ | m.p. 106-110° C. |
| 23 | $(CH_3)_3C-$ | $OSO_2CF_3$ | viscous oil |
| 24 | $(CH_3)_3C-$ | $OSO_2N(CH_3)_2$ | m.p. 135-140° C. |
| 25 | $(CH_3)_3C-$ | Br | |
| 26 | $(CH_3)_3C-$ | $NH_2$ | |
| 27 | $(CH_3)_2CH-$ | OH | m.p. 170-173° C. |
| 28 | $(CH_3)_2CH-$ | Cl | m.p. 76-78.5° C. |
| 29 | $CH_3CH_2CH-$<br>$CH_3$ | OH | m.p. 130-131.5° C. |
| 30 | $CH_3CH_2CH-$<br>$CH_3$ | Cl | $n_D^{20}$ 1.5460 |
| 31 | $(CH_3)_3C-$ | $OCOOCH_3$ | |
| 32 | $(CH_3)_3C-$ | $OCOOCH_2CF_3$ | |

Example 2

Synthesis of an intermediate:

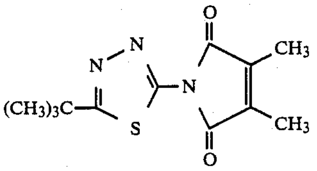

2-Amino-5-tert-butyl-1,3,4-thiadiazole (1.57 g) and 2,3-dimethylmaleic anhydride (1.51 g) were refluxed for 5 hours in glacial acetic acid (30 ml). After the reaction, acetic acid and the excess of the 2,3-dimethylmaleic anhydride were evaporated. The residue was dissolved in dichloromethane (50 ml), and the solution was washed with a 10% aqueous solution of potassium carbonate (20 ml), and dried over anhydrous magnesium sulfate. The solvent was evaporated to give the desired N-(5-tert-butyl-1,3,4-thiadiazol-2-yl)-2,3-dimethylmaleinimide (2.41 g), mp. 87°-91° C.

BIOLOGICAL TESTS

Comparative Compounds

E-1

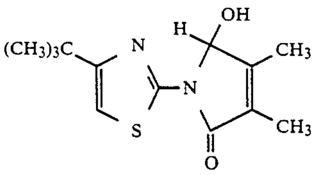

:

(described in Japanese Laid-Open Patent Publication No. 23,965/1978).

E-2

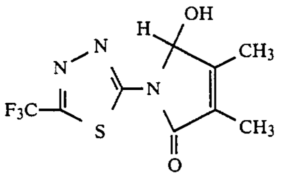

:

(described in Japanese Laid-Open Patent Publication No. 23,965/1978).

E-3

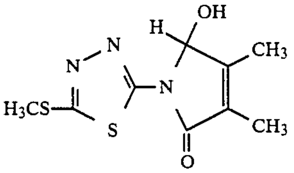

:

(described in Japanese Laid-Open Patent Publication No. 23,965/1978).

Example 3

Pre-emergence soil treatment test

Preparation of an active compound

Carrier: 5 parts by weight of acetone. Emulsifier: 1 part by weight of benzyloxy polyglycol ether.

A formulation of the active compound is obtained as an emulsifiable concentrate by mixing 1 part by weight of the active compound with the above amounts of the carrier and the emulsifier. A predetermined amount of the formulation is diluted with water to prepare a test chemical.

Testing Method

Seeds of corn were sown in pots (500 $cm^2$) filled with upland farm soil in a greenhouse, and soil containing seeds of goosefoot (*Chenopodium album*), barnyard grass (*Echinochloa crus-galli*) and wild amaranth (*Amaranthus lividus*) was put over the corn seeds to a depth of 1 cm.

One day after the sowing, a predetermined amount of the test chemical was sprayed uniformly onto the surface layer of the soil in the test pots.

Four weeks after the spraying, the herbicial effect and the degree of phytotoxicity to the crop (corn) were rated and evaluated on a scale of 0 to 5 as follows:

The herbicidal effect was evaluated as the percentage of weed killing based on that in the non-treated area on the following scale.

5: at least 95% (withered).
4: at least 80% but less than 95%.
3: at least 50% but less than 80%.
2: at least 30% but less than 50%.
1: at least 10% but less than 30%.
0: less than 10% (no effect).

The phytotoxicity to rice was evaluated by the phytotoxicity rate based on that in the non-treated area on the following scale.

5: at least 90% (fatal injury).
4: at least 50% but less than 90%.
3: at least 30% but less than 50%.
2: at least 10% but less than 30%.
1: more than 0% but less than 10%.
0: 0% (no phytotoxicity).

With respect to typical examples, the test results are shown in Table 2.

TABLE 2

| Compound No. | Amount of the active component (kg/ha) | Herbicidal effect A | Herbicidal effect B | Herbicidal effect C | Phyto-toxicity |
|---|---|---|---|---|---|
| 1 | 0.5 | 5 | 5 | 5 | 0 |
| | 0.25 | 5 | 5 | 4 | 0 |
| Comparison | | | | | |
| E-1 | 0.5 | 1 | 1 | 0 | 0 |
| | 0.25 | 0 | 0 | 0 | 0 |
| E-2 | 0.5 | 1 | 2 | 0 | 0 |
| | 0.25 | 0 | 1 | 0 | 0 |
| E-3 | 0.5 | 1 | 1 | 0 | 0 |
| | 0.25 | 0 | 0 | 0 | 0 |

A: wild amaranth
B: goosefoot
C: barnyard grass

Example 4

Foliar treatment test on upland weeds

In a greenhouse, seeds of corn were sown in pots (500 $cm^2$) filled with upland farm soil, and soil containing seeds of wild amaranth and goosefoot were put over them to a depth of 1 cm.

The plants were grown for 14 days after the sowing, and a predetermined amount of a test chemical prepared as in Example 3 was uniformly sprayed over the plants in the pots.

Four weeks after the spraying, the herbicidal effect and the degree of phytotoxicity to the crop (corn) were examined on the same standards as in Example 3. With respect to typical examples, the results are shown in Table 3.

TABLE 3

| Compound No. | Amount of the active component (kg/ha) | Herbicidal effect A | Herbicidal effect B | Phyto-toxicity |
|---|---|---|---|---|
| 1 | 0.5 | 5 | 5 | 0 |
| | 0.25 | 5 | 5 | 0 |
| Comparison | | | | |
| E-1 | 0.5 | 2 | 2 | 0 |
| | 0.25 | 1 | 1 | 0 |
| E-2 | 0.5 | 3 | 3 | 0 |
| | 0.25 | 1 | 2 | 0 |
| E-3 | 0.5 | 2 | 2 | 0 |
| | 0.25 | 1 | 1 | 0 |

A and B: the same as the footnote to Table 2.

It will be understood that the specification and examples are illustrative but not limitative of the present invention and that other embodiments within the spirit and scope of the invention will suggest themselves to those skilled in the art.

We claim:

1. A compound of the formula
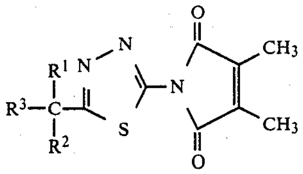
wherein
$R^1$ represents a hydrogen atom or an alkyl group having 1 to 4 carbon atoms and
$R^2$ and $R^3$ each represent an alkyl group having 1 to 4 carbon atoms or a haloalkyl group having 1 to 4 carbon atoms or together may form a $C_2$–$C_6$-alkylene group which may be substituted by halogen.
* * * * *